(12) United States Patent
Morris et al.

(10) Patent No.: US 6,390,992 B1
(45) Date of Patent: May 21, 2002

(54) INTRALUMINAL DEVICE WITH LUBRICIOUS SURFACE

(75) Inventors: Joy E. Morris, Santa Clara; Edwin Petrus Mahieu, Murrieta, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 08/825,411

(22) Filed: Mar. 27, 1997

Related U.S. Application Data

(63) Continuation of application No. 08/437,440, filed on May 5, 1995, now abandoned.

(51) Int. Cl.$^7$ .............................................. A61M 25/00
(52) U.S. Cl. .................................. 600/585; 604/164.13
(58) Field of Search ....................... 128/772; 604/164, 604/282, 265, 164.07, 164.08, 164.13; 600/585, 300

(56) References Cited

U.S. PATENT DOCUMENTS

| | | | | |
|---|---|---|---|---|
| 4,534,363 A | * | 8/1985 | Gold .......................... 128/772 |
| 4,666,437 A | * | 5/1987 | Lambert ..................... 604/265 |
| 4,721,117 A | * | 1/1988 | Mar et al. ................... 128/772 |
| 4,759,748 A | * | 7/1988 | Reed ............................ 604/95 |
| 4,813,434 A | * | 3/1989 | Buchbinder et al. ........ 128/772 |
| 4,925,668 A | * | 5/1990 | Khan et al. ............. 604/265 X |
| 5,026,607 A | * | 6/1991 | Kiezulas ................. 604/265 X |
| 5,061,738 A | * | 10/1991 | Solomon et al. ........ 604/265 X |
| 5,069,217 A | | 12/1991 | Fleischhacker, Jr. ........ 128/657 |
| 5,077,352 A | * | 12/1991 | Elton ..................... 604/265 X |
| 5,091,205 A | * | 2/1992 | Fan ........................ 604/265 X |
| 5,135,516 A | * | 8/1992 | Sahatjian et al. ............ 604/265 |
| 5,179,174 A | * | 1/1993 | Elton ..................... 604/265 X |
| 5,242,428 A | * | 9/1993 | Palestrant .................... 604/265 |
| 5,312,356 A | * | 5/1994 | Engelson et al. ........... 604/164 |
| 5,331,027 A | * | 7/1994 | Whitbourne ............ 604/265 X |
| 5,407,590 A | * | 4/1995 | Salvia .......................... 252/12 |
| 5,433,200 A | * | 7/1995 | Fleischhacker, Jr. ........ 128/657 |
| 5,441,488 A | * | 8/1995 | Shimura et al. ............ 604/265 |
| 5,443,455 A | * | 8/1995 | Hergenrother et al. .. 604/265 X |
| 5,531,715 A | * | 7/1996 | Engelson et al. ........... 604/265 |

FOREIGN PATENT DOCUMENTS

| | | |
|---|---|---|
| EP | 0 343 509 | 11/1989 |
| EP | 0 495 299 A1 | 7/1992 |
| EP | 0 631 792 A1 | 1/1995 |
| JP | 6 121828 | 8/1994 |
| WO | WO 93/15781 | 4/1993 |
| WO | WO 96/03163 | 2/1996 |

OTHER PUBLICATIONS

Dicronite Internet Home Page; pp. 1–2; located at www.dicronite.com.*

Dicronite Trademark Registration Information; obtained from www.trademarks.uspto.gov.*

* cited by examiner

*Primary Examiner*—Sam Rimell
(74) *Attorney, Agent, or Firm*—Fulwider Patton Lee & Utecht, LLP

(57) ABSTRACT

This invention comprises a guidewire with a tenacious lubricious coating on its surface comprising a finely divided lubricious particulate. The coatings of this invention have a thickness of not more than about 0.00002 inch, a coefficient of friction of not more than about 0.030 and a hardness not less than about 1.0 Mohs. Preferably, the surface coating comprises a monomolecular layer of particulate tungsten disulfide. The guidewire of this invention incorporates an improved distal tip configuration comprising a flexible elongate core member which has at least one tapered section at its distal extremity and a flattened distal portion. The distal portion has two or more flattened regions having cross-sectional areas which decrease in the distal direction. A flexible helical coil is attached to the core member and comprises three or more distinct regions, each having increasing coil spacing in the distal direction. Preferably, the entire length of the guidewire proximal to the helical coil has the lubricious particulate surface coating of the invention.

8 Claims, 2 Drawing Sheets

INTRALUMINAL DEVICE WITH LUBRICIOUS SURFACE

This is a continuation of application Ser. No. 08/437,440 filed on May 5, 1995 now abandoned.

BACKGROUND OF THE INVENTION

This invention directed to the field of elongated intraluminal devices having surfaces with lubricious coatings, and, in particular, to a low friction guidewire having an improved distal tip design.

Guidewires are well known in the art and have been the subject of continual improvement. One direction of improvement has centered on reducing the surface friction of the guidewire to facilitate insertion and advancement of the guidewire and the subsequent introduction of a vascular device threaded over it. Much of the innovation has centered on laminating a low friction, polymeric material onto the surface of the guidewire. Polytetrafluoroethylene (PTFE) and various hydrophilic polymers, such as polysiloxane, are examples.

In addition to guidewires, virtually all intraluminal devices may benefit from having a lubricious surface to facilitate insertion and guidance to the desired intraluminal destination. Reducing friction also minimizes luminal trauma caused by insertion of these devices, particularly in blood vessels such as coronary arteries. Often, multiple intraluminal devices are used during a procedure such as angioplasty or atherectomy, requiring coaxial or rotational movement with respect to each other. In such instances, the outer surface of the device, whether it interacts with the interior of another intraluminal device or the vasculature, and device lumens that receive other intraluminal devices are candidates for a lubricious surface. As with guidewires, much has been done with the prior art polymer layers to produce intraluminal devices having low friction surfaces. Although the prior art has achieved certain successes, a number of drawbacks are associated with the use of polymer layers. Generally, elongated intraluminal devices are quite long and have a small outer diameter. For example, a typical guide wire is 175 cm long, but can be 300 cm or longer, and has an outer diameter of between 0.010 and 0.050 inch. Providing such devices with a uniform coating is technically difficult and correspondingly expensive. Further, intraluminal devices having layers comprising polymeric materials require extreme care in handling as the layers are very susceptible to abrasion and other damage.

There remains a need for intraluminal devices having a tenacious effective lubricious surface without the drawbacks associated with the prior art techniques. In particular, there is a need for a low friction guidewire with an improved distal tip. This invention satisfies these and other needs.

SUMMARY OF THE INVENTION

This invention is directed to elongated intraluminal devices that have a tenacious lubricious coating on their surface comprising a finely divided lubricious particulate. The lubricious particulate is preferably selected from the group consisting of tungsten disulfide, molybdenum disulfide and the like. The coatings of this invention have a thickness of not more than about 0.00002 inch and generally form a monomolecular layer. Preferably, the coefficient of friction is not more than about 0.030. The coatings also have a hardness not less than about 1.0 Mohs. Preferably, the surface coating comprises a monomolecular layer of particulate tungsten disulfide. The lubricious particulate is preferably not more than about 0.5 micron in maximum diameter.

The coatings of this invention offer significantly improved characteristics over the prior art polymer coatings. One significant advantage is that the lubricious particulate coatings are much thinner than the polymer coatings. Preferably, the lubricious particulates form an irreversible bond with the substrate but do not bond each other. Accordingly, they form a very uniform monomolecular layer. Since the particulate coatings are tenacious and relatively hard, they are more durable than typical polymeric coatings. The particulate coatings also offer at least equivalent coefficients of friction as the polymeric coatings.

In addition to the tenacious lubricious particulate surface coating, the guidewires of this invention incorporate an improved distal tip configuration designed to maximize flexibility while maintaining torsional and columnar strength. The guidewire comprises a flexible elongate core member that has at least one tapered section at its distal extremity and a flattened distal portion. The distal portion has two or more flattened regions having cross-sectional areas which decrease in the distal direction. The maximum diameter of the guidewire is not more than about 0.03 inch, and preferably is not more than about 0.015 inch.

A flexible helical coil of suitable material wraps around and is attached to the core member. The helical coil comprises three or more distinct regions, each having increasing coil spacing in the distal direction to provide correspondingly greater flexibility. The most distal region of the coil is secured to the distal portion by suitable means, such as solder, to form a rounded plug at the distal tip. The most proximal end of the coil is secured to the core member by suitable means such as solder.

This distal tip configuration with variable coil spacing provides a smooth transition from a relatively stiff proximal section to a very flexible distal section while maintaining adequate columnar and torsional strength. The rectangular cross sections of the flattened distal portion bias the flexibility of the coil in the direction normal to the major dimension of the rectangular cross section.

Preferably, the entire length of the guidewire proximal to the helical coil has the lubricious particulate surface coating of the invention. In others, a portion of the guidewire proximally adjacent the helical coil may have an additional layer of a conventional lubricious polymer under the lubricious particulate coating.

DETAILED DESCRIPTION OF THE INVENTION

Figure 1:
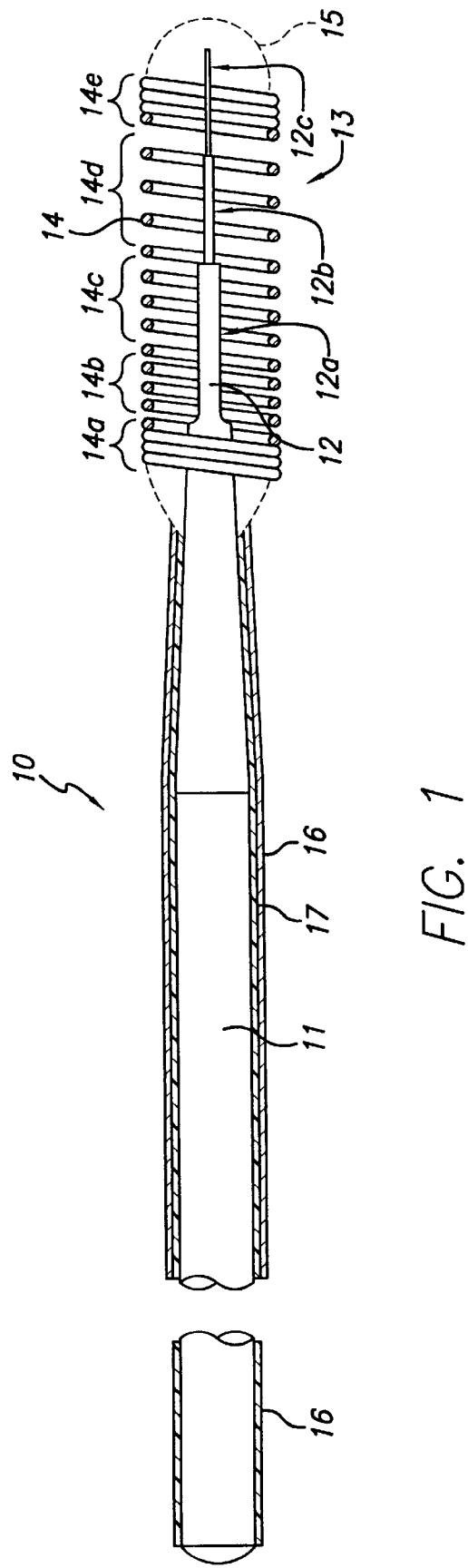
FIG. 1 illustrates an elevational view, partially in section, of a guidewire embodying features of the invention.

FIG. 1 illustrates a guidewire 10 having features of this invention that generally include an elongated core member 11 and a flattened distal portion 12. The distal end of guidewire 10 has an improved shapeable distal tip 13 that comprises the distal portion 12 and a flexible helical coil 14. Helical coil 14 is attached either to the core member 11 and distal portion 12 as depicted in FIG. 1 or to distal portion 12 alone. The distal end of shapeable distal tip 13 has a rounded end 15, preferably formed by a solder plug securing helical coil 14 to distal portion 12.

Cylindrical portion 11 has a tenacious lubricious particulate surface coating 16. Preferably, the tenacious particulate coating 16 comprises a monomolecular layer of tungsten disulfide particulate. Tenacious particulate coating 16 generally runs the length of the core member 11. In some embodiments, a section of guidewire 10 proximally adjacent helical coil 14 may have an additional coating of a conventional low friction polymer 17 over the tenacious particulate coating 16. The low friction polymer may be polysiloxane, such as Microglide®, registered to Advanced Cardiovascular Systems, Inc. of Santa Clara, Calif., PTFE or any other suitable lubricious surface. In this embodiment, the distal 40 cm of guidewire 10, starting behind helical coil 14, has an additional coating of low friction polymer 17 under tenacious coating 16. Typically, helical coil 14 does not have a friction-reducing coating because the higher friction aids guidewire placement by anchoring the end of the guidewire 10 against a vessel wall at a vessel junction.

The distal portion 12 is generally formed by flattening the distal extremity of the elongated core member 11. Distal portion 12 has a number of regions 12a, 12b and 12c have rectangular transverse cross-sectional areas which decrease in the distal direction: region 12a is about 0.4 cm long and is about 0.002 inch in the major dimension of its cross section; region 12b is about 0.2 cm long and is about 0.0015 inch in the major dimension of its cross section; and region 12c is about 1.4 cm long and is about 0.001 inch in the major dimension of its cross section. In other embodiments, the distal portion 12 comprises at least two regions which have cross-sectional areas that decrease in the distal direction with a major cross-sectional dimension between about 0.003 and 0.0015 inch and a second region having a major cross-sectional dimension between about 0.002 and 0.0005 inch. The flattened configuration serves to bias the flexibility of shapeable distal tip 13 in the direction normal to the major dimension of the rectangular cross section. The decreasing cross-sectional area allows the distal portion to have a variety of flexible characteristics including a smooth transition in flexibility along its length.

Helical coil 14 has a number of regions 14a, 14b, 14c, 14d and 14e which have different coil spacing. Preferably, in this embodiment, regions 14a and 14e have a tight stacked arrangement wherein the adjacent coils touch. Regions 14b, 14c and 14d have progressively greater spacing between the adjacent coils; in this embodiment region 14b has been stretched ten percent of its unstretched length. Regions 14c and 14d have twenty and thirty percent stretch, respectively. In other embodiments, the helical coil has at least three regions of having increased coil spacing in the distal direction to provide a more flexible and less traumatic distal tip 13. Regions 14a and 14e are secured to the distal end of guidewire 10. Preferably, region 14a is attached to the core member 11 adjacent the flattened distal portion 12 and region 14e is attached to the distal end of distal portion 12c, forming rounded end 15. Helical coil 14 may be attached in any suitable manner; in general soldering is preferred. This configuration serves to transmit torque through helical coil 14. The progressively greater spaced regions of helical coil 14 allow the distal tip 13 to have improved shapeability and to have a wide range of flexible characteristics, in general giving it more flexibility than prior art coil designs.

For coronary applications, guidewire 10 may have a length between about 130 cm and 300 cm, but preferably is about 175 cm long. In this embodiment, the distal 2 to 4 cm of core member 11 is continuously tapered. The helical coil 14 is about 1 to 10 cm, preferably about 1.5 to 3.5 cm, in length and it has an outer diameter of about 0.01 to 0.02 inch and the distal portion 12 is about 2 cm long.

One suitable tenacious particle coating 16 comprises tungsten disulfide in the form of Dicronite®, that may be obtained from Dicronite® Dry Lube, Northwest of Santa Clara, Calif. Dicronite® transmigrates into the molecular structure of the substrate, forming an irreversible bond with metals and most plastics but does not bond to itself. It forms a very uniform film of about 0.00002 inch, which may be burnished or polished to a thickness of about 0.000015 inch.

Figure 2:
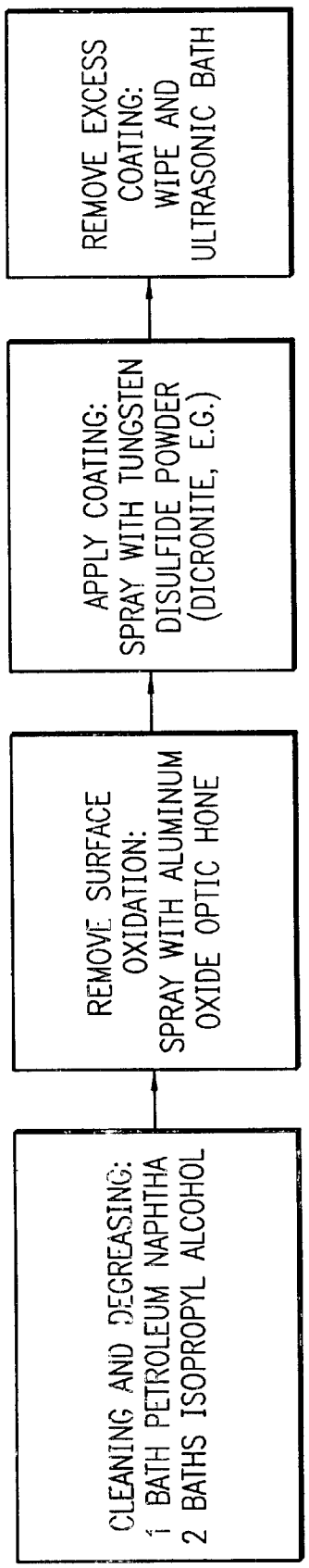
FIG. 2 is a schematic diagram representing the process of applying a coating to an intraluminal device according to this invention.

Applying Dicronite® to an intraluminal device generally comprises the steps of cleaning the device with one bath of petroleum naphtha and two baths of isopropyl alcohol, spraying the device with an aluminum oxide optic hone to remove any surface oxidation and then spraying on the Dicronite® with an air carrier. Any excess Dicronite® may be removed in a subsequent ultrasonic bath. FIG. 2 represents a schematic diagram of these steps.

The invention has been described herein primarily with reference to presently preferred embodiments comprising tungsten disulfide coatings applied to coronary artery guidewires. However, it should be recognized that various other inorganic lubricious coatings, such as molybdenum disulfide, may be used. Other modifications and improvements can be made to the invention and such coatings may be applied to a variety of intraluminal products including electrophysiology devices, atherectomy catheters and the like without departing from the scope thereof.

What is claimed is:

1. A guidewire comprising:
   a) an elongated metallic core member having proximal and distal ends and an exterior surface;
   b) a tenacious lubricious discrete coating which is formed of a substantially monomolecular layer finely divided lubricious particulate and which has a thickness of not more than 0.00002 inches, on the exterior surface of the core member; and
   c) a flexible helical coil having proximal and distal ends disposed over at least a distal part of the core member.

2. The guidewire of claim 1 wherein the tenacious lubricious coating is selected from the group consisting of tungsten disulfide and molybdenum disulfide.

3. The guidewire of claim 2 further comprising an additional reduced friction layer over the tenacious lubricious coating on the core member.

4. The guidewire of claim 1 wherein the helical coil further comprises at least three expanded coil regions, each region having a coil spacing which is greater than the coil spacing of the region proximal thereto.

5. The guidewire of claim 4 comprising a first region having between 5 and 15 percent stretch, a second region between 10 and 30 percent stretch and a third region having between 20 and 40 percent stretch.

6. The guidewire of claim 1 wherein the elongated core member has a flattened distal portion with at least two regions, each region having a transverse cross-sectional area which decreases towards the distal end.

7. The guidewire of claim 6 comprising a first core portion region having a major cross-sectional dimension between about 0.003 and 0.0015 inch and a second region having a major cross-sectional dimension between about 0.002 and 0.0005 inch.

8. The guidewire of claim 1 wherein the helical coil further comprises at least three expanded coil regions, each region having a coil spacing which is greater than the coil spacing of the region proximal thereto and wherein the core member has a flattened distal portion with at least two regions, each region having a transverse cross-sectional area which decreases towards the distal end.

* * * * *